United States Patent [19]

Seager et al.

[11] Patent Number: 5,199,442
[45] Date of Patent: Apr. 6, 1993

[54] APPARATUS FOR REDUCTION OF SPASTICITY IN MALE AND FEMALE PATIENTS HAVING SPINAL CORD INJURY AS WELL AS OBTAINING SEMEN FROM MALES BY STIMULATION OF EJACULATORY NERVES

[76] Inventors: Stephen W. J. Seager, 10301 Norton Rd., Potomac, Md. 20854; Lauro S. Halstead, 3522 Woodbine St., Chevy Chase, Md. 20815

[21] Appl. No.: 701,815

[22] Filed: May 20, 1991

[51] Int. Cl.5 .......................... A61N 1/05; A61N 1/38
[52] U.S. Cl. .................................... 128/788; 128/734; 128/419 S; 128/421
[58] Field of Search ................... 128/788, 784, 419 S, 128/736, 401, 421, 422

[56] References Cited

U.S. PATENT DOCUMENTS

| | | | |
|---|---|---|---|
| 2,126,257 | 8/1938 | Hird | 128/788 |
| 2,808,834 | 10/1957 | Marden | 128/419 S |
| 4,124,028 | 11/1978 | Gallo | 128/422 X |
| 4,227,535 | 10/1980 | Connor | 128/401 |
| 4,542,753 | 9/1985 | Brenman et al. | 128/788 |
| 4,564,024 | 1/1986 | Wohler, Jr. | 128/419 S |
| 5,117,840 | 6/1992 | Brenman et al. | 128/788 |

FOREIGN PATENT DOCUMENTS 2552663  4/1985  France ............................... 128/788

Primary Examiner—Lee S. Cohen
Attorney, Agent, or Firm—J. Gibson Semmes

[57] ABSTRACT

Apparatus for treatment of spasticity by electrical stimulation in male and female patients having spinal cord injury. The apparatus is likewise adapted to stimulate ejaculatory nerves in the male through ejaculation and is characterized by an electronic stimulator which delivers current by rectal probe to the prostate and seminal vesicle glands in serial variance of since wave voltage. In both male and female treatment of spasticity, substantially similar apparatus is employed.

2 Claims, 3 Drawing Sheets

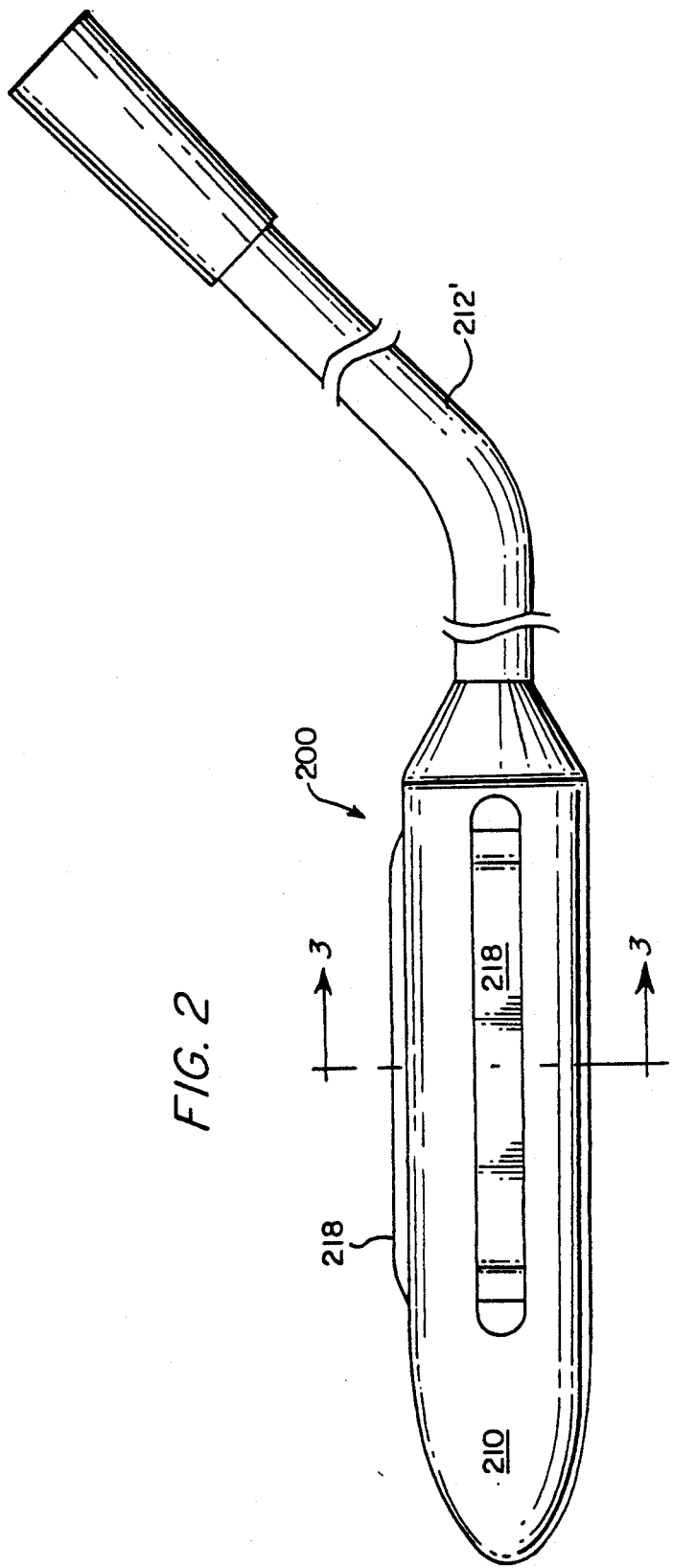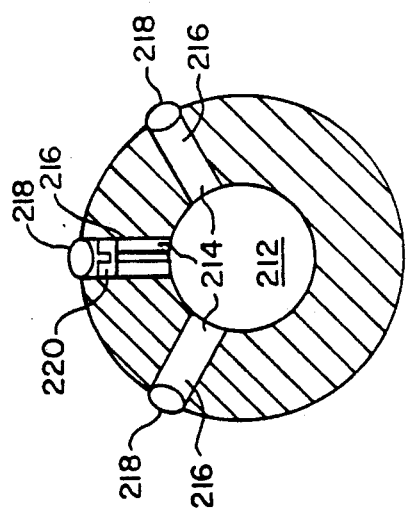

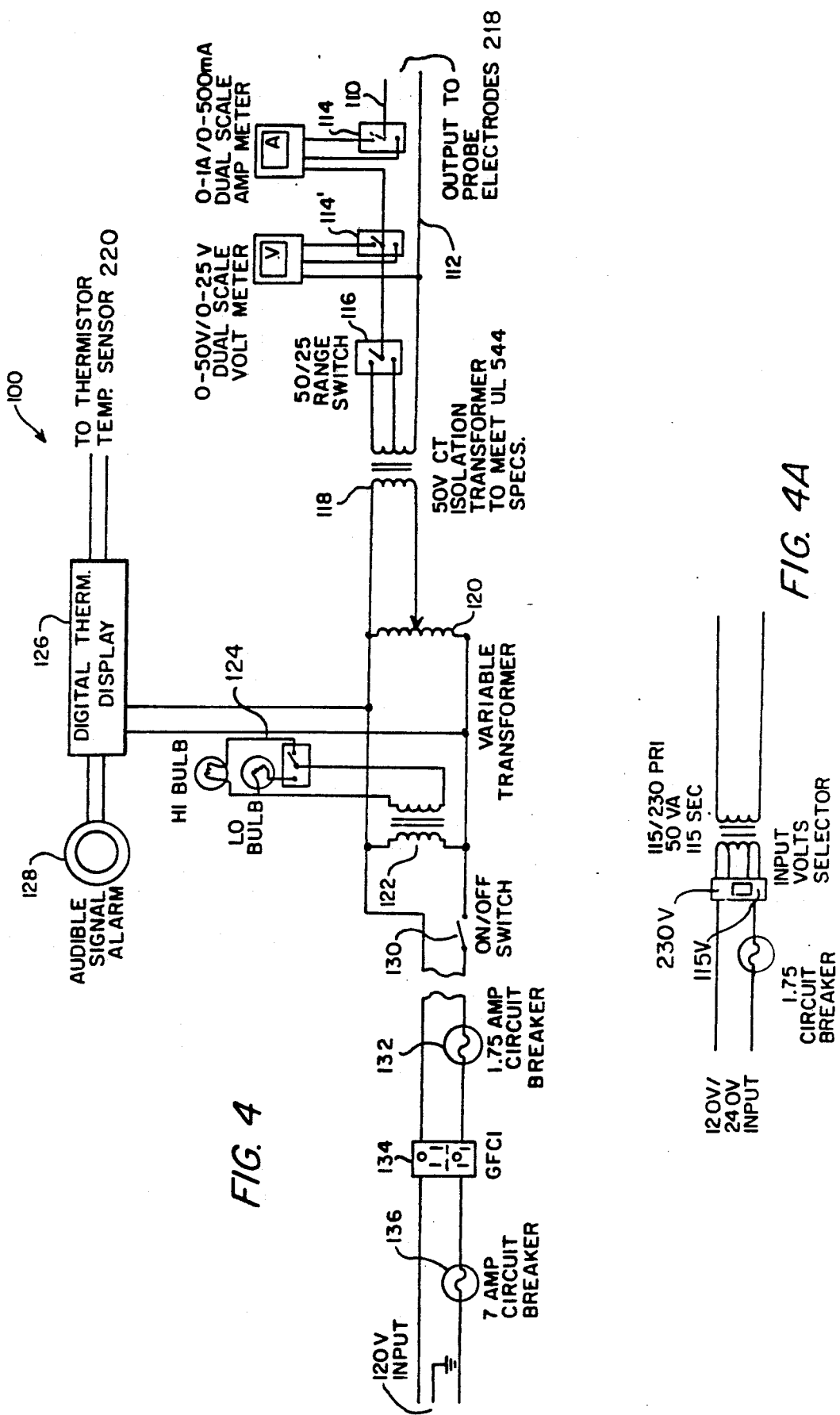

APPARATUS FOR REDUCTION OF SPASTICITY IN MALE AND FEMALE PATIENTS HAVING SPINAL CORD INJURY AS WELL AS OBTAINING SEMEN FROM MALES BY STIMULATION OF EJACULATORY NERVES

BACKGROUND OF THE INVENTION

Sexual dysfunction in males suffering from spinal cord injury, SCI and other neurological conditions such as multiple sclerosis is well known. Impotence is the most common problem, but inability to ejaculate may also occur. Whereas those suffering from impotency may obtain penile prosthesis implantation or intracavernous injection therapy, those with anejaculation, nonetheless, are infertile. Until the present invention, no therapy has been available for this condition. To reduce spasticity in both males and females afflicted with SCI is likewise an objective of invention. Similar problems arise in females suffering from SCI.

Normal ejaculatory function in the human male implies a coordinated sequence of smooth and striate muscular contractions to promote projectile, antegrade transport of seminal fluid. This process begins with transmission of afferent nerve stimuli via the internal pudendal nerve from the penile shaft to higher centers. To complete the ejaculatory reflex efferent stimuli are transmitted from the anterolateral columns of the spinal cord and emerging from the thoracolumbar level to comprise a hypogastric or sympathetic plexus. From the interior mesenteric ganglion short adrenergic postganglionic fibers terminate in the seminal vesicles, vasal ampullae, and bladder neck. Sympathetic innervation of the seminal vesicles results in seminal emission into the posterior urethra. Appropriately timed bladder neck closure prevents retrograde passage of this semen bolus, which is propelled in the antegrade direction by clonic contracts of the bulbocavernosus and ischiocavernosus muscles of the pelvic floor. Electrojaculation studies in spinal cord transected primates indicate that the presence of postganglionic short adrenergic fibers are the minimal requirement for electrostimulated ejaculation. The fact that emission can be successfully electrostimulated by rectal probe electrode, up to two years following cord abation, indicates that the normal ejaculatory reflex can be bypassed.

Retrograde ejaculation has been noted as a constant finding in electroejaculatory stimulation by rectal probe electrode. In contrast to its action in normal ejaculation, the electrostimulated bladder neck must either be unresponsive or must undergo delayed closure.

Electroejaculation by rectal probe electrode has, in a short period, impacted significantly on the fertility potential of spinal cord injured men. This specific group, previously considered "sterile", can now undergo semen procurement predictably and safely. Importantly, they may benefit from the same sperm assessment procedures and in-vitro sperm enhancement techniques as applied to the general population seeking infertility testing and treatment.

Whereas electroejaculation has been used for inducing emission of semen both in animals and in humans, the present technique employs an electrical probe which is placed in the rectum. The probe is connected to a combination electrical stimulator and temperature meter and upon order, current is delivered to the probe in a sine-wave pattern. During stimulation, carefully disposed bipolar electrodes are directed anteriorly to stimulate those short neurons entering the ejaculatory organs, which lie anterior to the rectum. As the electrical stimulus is being applied, the bulbous and pendulous urethra are "milked" to encourage an antegrade ejaculate. The bladder is irrigated with modified Hamm's F-10 solution to retrieve the maximum number of sperm. Hitherto, the most widely used successful application of electroejaculation has been in spinal-cord-injury patients. It has also been used to obtain semen after retroperitoneal lymph node dissection (RPLND), MS, diabetes neurol tube defect, and other neurogenic physiogenic conditions.

After experimentation with electroejaculation in various species of animals and following many years of experience working with animals, a study was initiated in 1985 using this technique to obtain semen in neurologically impaired men. The first subjects were men with spinal cord injury, hereinafter SCI; later electroejaculation was applied to men suffering from other neurological conditions; these include men who have had a retroperitoneal lymph node dissection, and those suffering from multiple sclerosis, adult diabetes and other non-specific anejaculatory disorders. The main research effort has been directed towards those with SCI. To date over 3,000 electroejaculation procedures have been applied to 250 men. The levels of injury for these SCI men have ranged from C3 to L2 with the majority being in the thoracic area and the injuries being complete. The overall success rate in obtaining an ejaculate, be it antigrade or retrograde, has been in the order of 80%. Working with those suffering from thoracic SCI lesions, there is approximately a 90% success rate in obtaining an ejaculate. If this latter group, some 75% will have an ejaculate considered sufficient quality for artificial insemination by inter-uterine deposition of washed spermatoza. Using the hereinafter described equipment and technique with SCI men, there have been 40 reported pregnancies in the U.S. Europe. Also a live birth in a couple where the husband has multiple sclerosis and a further two where the husbands had retroperitoneal lumph node dissections following surgical treatment for testicular cancer.

The method and apparatus are likewise effective in treating both males and females having SCI wherein spasticity may be effectively reduced for significant after treatment periods of time. See Example #2, hereinafter.

SUMMARY OF INVENTION

The electroejaculation equipment employed herein includes a 60 Hz sine wave stimulator which is connected to a probe which is to be placed in the rectum. Three raised electrodes of the probe are secured longitudinally on the ventral surface of the probe. At least one thermocouple indicator beneath the surface of one electrode indicates the patient's rectal temperature during the procedure.

In practice the lubricated probe is inserted into the rectum and placed adjacent both prostrate and seminal vesicle glands. Patients are placed in lateral decubitus and anascopy performed pre and post stimulation, for signs of rectal mucosal alteration. Blood pressure and other vital signs are monitored during the procedure, while the amount of stimulation applied may range from 0 to 35 volts and 0 amp to 700 milliamps. The current is administered by increases of the voltage in a specific pattern hereinafter defined. Careful notation is made of the number of stimulations and the response of the patient in relation to volrage administered. In most instances, ejaculation commenced prior to full erection and continued as full erection was achieved. The patient's bladder was normally emptied by a penile catheter, pre and post procedure. A suitable sperm medium was used to flush the bladder when post procedure catheterization is done.

Substantially the same practice is applied by both male and female patients afflicted with SCI to reduce spasticity.

BRIEF DESCRIPTION OF THE DRAWINGS

FIG. 2 is a partial view in side elevation of the probe illustrated in FIG. 1.

FIG. 3 is a vertical section view of the probe of FIGS. 1 and 2.

FIG. 4 is a circuit diagram of the electric circuit employed in the invention which combines the elements depicted in the preceding drawings. FIG. 4A is an alternate circuit for dual voltage.

DESCRIPTION OF PREFERRED EMBODIMENTS

Figure 1:
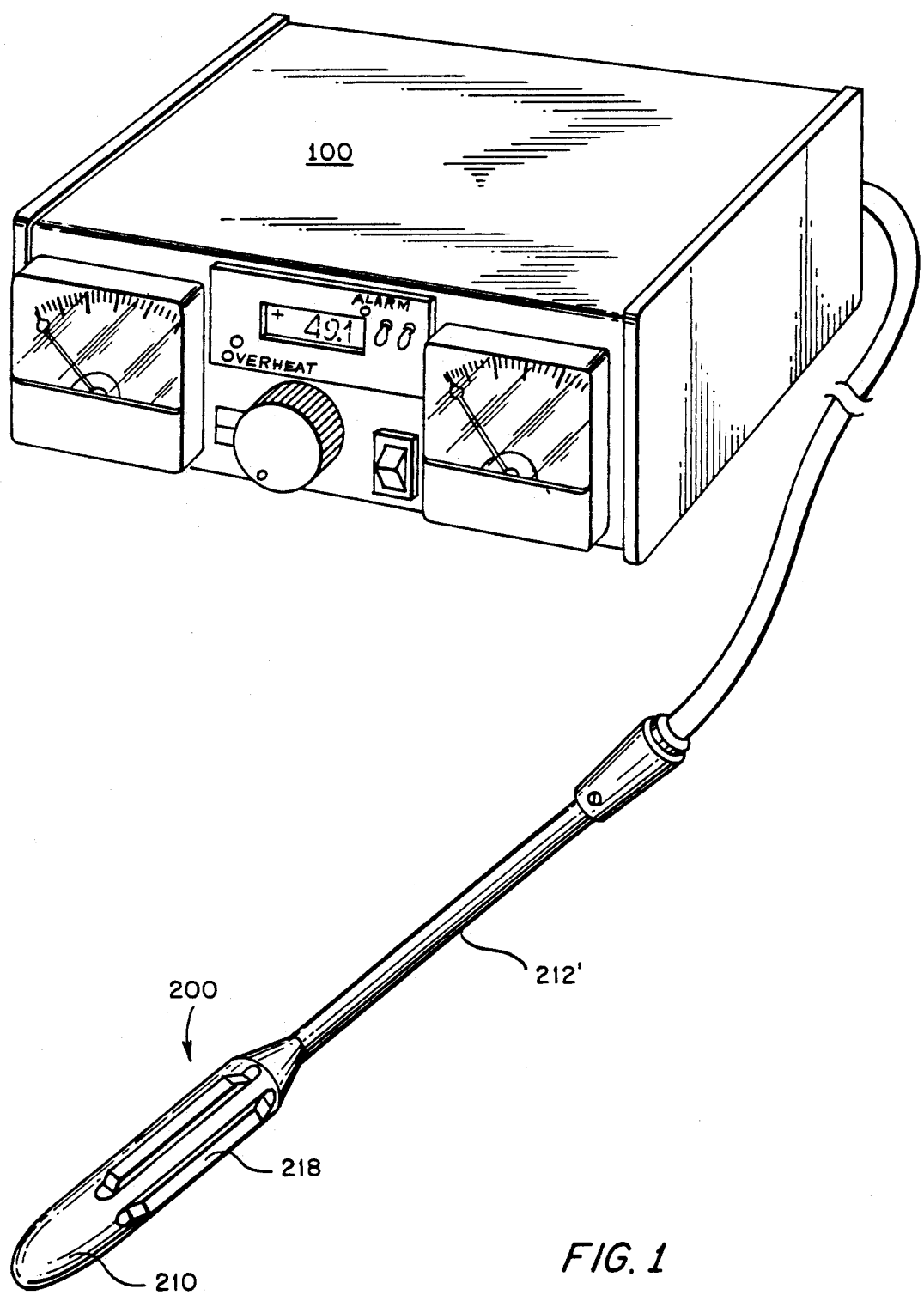
FIG. 1 is a prespective of the system apparatus incluiding stimulator control and its associated probe.

To conduct the present practice of eletroejaculation on neurologically impaired men, the equipment defined herein is utilized. It is best illustrated in FIG. 1, wherein the following components are combined. The same equipment is utilized in treatment to reduce spasticity in both male and female patients likewise impaired.

An electrical power supply stimulator and temperature meter 100 is adapted by electronic circuitry to deliver current in a 60 Hz sine wave pattern. This stimulator and control is interconnected with an elongated rectal probe 200 which is preferably of circular cross-section, the probe having bipolar metal electrodes set therein and at least one temperature probe or sensor disposed therebetween. Variation in overall size of the rectal probe will be required as the practice may vary as between male female patients.

As indicated, elongated rectal probe 200 is best shown in FIGS. 2 and 3. The probe itself consists of a substantially solid dielectric composition such as a polyvinyl chloride, having a probe body 210, the center of which contains, from the proximal end, an axially aligned channel 212, said channel having interconnection with plural conduits 214, emanating radically therefrom. These conduits terminate in longitudinally extending cavities 216, each cavity forming a repository for one of three electrically conductive bipolar metal electrodes 218, all being raised exteriorly and set within the elongated ventral surface of the rectal probe 200. See FIG. 2. The channel 212 has interconnection with the rigid conductor 212' which forms a housing for respective conductors emanating therefrom to join the corresponding electrical connections from the stimulator. See electronic circuit FIG. 4. As will be apparent from reference to FIG. 3, appropriate cavities and connecting channels are provided to interconnect the temperature responsive thermistor 220 with the interior of the probe, from beneath its ventral surface to interconnect once again with the circuit meter conductor. The diameter of the probe may vary from 2.7 to 3.2 cm. The rigid conductor extension is provided with axially aligned orienting guide indices at the free end thereof to indicate the disposition of the electrodes relative to the spinal column of the patient. Likewise, the conductor extension is provided with rectal insert gradients ranging from one to three centimeters, as shown.

The circuit which has interconnection with the probe is designed to generate stimulation in the amount of 0–35 volts and 0 amp–700 milliamps. See FIG. 4. FIG. 4A illustrates a partial substitute circuit, adaptable to dual voltage power source.

OPERATION

On the present domestic U.S.A. model known as Model 12, there is a convenience receptacle provided, GFCI type 134, protected by a 7 amp circuit breaker 136; thus the receptable can supply 600 watts conservatively rated. The 1.75 amp circuit breaker 132 protects the rest of the instrument in the event of a short or overload. The on/off switch 130 is used to turn the unit on and off. The 6.3 volt transformer 122 is used to power the indicator lamps in the pushbutton range switch 116 which may also comprise a 4 pole, double throw type. It controls four functions: 1) indicator bulb #1 and #1; 2) main transformer output, 3) voltmeter high or low scale, and 4) ampmeter 124 high or low scale. The purpose of two ranges is to have accurate (mid-scale) meter readings over a wide range of output levels. The digital temperature display 126 is powered by 115 volts and has an internal power supply. It is a self-contained unit that performs the following functions: 1) displays the probe electrode temperature, 2) has an adjustable alarm which is set by pushing the set button and turning the adjustment screw (the alarm set point will be displayed as long as the set button is pushed). If the measured temperature should rise above set point, an audible signal 128 is sounded and an indicator lamp marked "DANGER, OVERHEAT" will light on the face of the display. The operator may temporarily disable the audible signal by pushing the "MUTE" button. This function resets itself if the temperature falls below set point, or if the power is turned off and on. The indicator lamp remains on even if the mute feature is used as long as the temperature remains above set point.

Besides powering the auxillary equipment such as temperature monitoring, the 115 volt supply powers the variable transformer 120. The knob on this is the control used to vary the output from 0 to maximum. The output from this feeds the isolation transformer 118. This reduces the output to 50 volts maximum or 25 volts maximum if the center tap is used (low range switch position). This transformer was specially manufactured to meet the requirements of UL spec 544 for patient contact medical use. It has the special insulation required to meet certain high voltage tests, intended to insure that the patient is well isolated from full line voltage. The hi/lo range selection function of the pushbutton switch is accomplished using the center tapped output of this transformer, then the output parameters of voltage and current are monitored by the two meters and the output leads 110 and 112, is delivered to the patient via the cord and rectal probe. The meters have high and low scales and these are selected by the push button switch poles labeled 114—114' and 116 in the drawing. The four functions of the pushbutton switch are coordinated so that when the button is in, the red half of the screen marked "50 VOLTS" glows, the full (50 volt) output of the transformer 118 is selected, the high (50 volt) scale of the voltmeter is selected and the high (1 amp) scale of the ampmeter is selected.

The overseas dual input voltage model is identical to the previously discussed model except for the power input area of the unit. The GFCI receptacle is omitted and the associated 7 amp circuit breaker is omitted also. There is still the 1.75 amp circuit breaker. There is an input voltage selector switch marked with a 115 v and 230 v position. This is connected to an extra transformer with a dual primary to accomplish the dual input selection. See FIG. 4A.

METHOD OF STIMULATION—EXAMPLE #1

The lubricated probe is inserted into the rectum and placed adjacent the prostate and seminal vesicle glands whereby the electrodes and thermocouples lie contiguous the glands. The patients are placed in lateral decubitus, anascopy being performed pre and post stimulation for signs of rectal mucosal alteration. Blood pressure and other vital for signs are monitored during the procedure. In those men who have a T7 injury or above and who may suffer autonomic dysreflexia during the stimulation period, nifedipine 10–50 mg. may be administered sublingually 15 minutes prior to the start of the procedure, to control any undue rise in blood pressure.

The amount of stimulation used in the method ranges from 0 to 35 volts and 0 amp to 700 milliamps. The current is administered by increases of the voltage in a specific pattern. Careful notation is made of the number of stimulations and the response of the patient in relation to voltage administered. In most instances, ejaculation commenced prior to full erection and continued as full erection was achieved. The patient's bladder is normally emptied by a penile catheter, pre and post procedure. A suitable sperm medium is used to flush the bladder when a post procedure catheterization was done. In studies to date, using this equipment and technique with SCI men, there have been 25 reported pregnancies (18 live births) in the U.S. Also a live birth in a couple where the husband is afflicted with multiple sclerosis and a further two where the husbands had retroperitoneal lymph node dissections following surgical treatment for testicular cancer.

Whereas the first subjects were men with spinal cord injury or SCI, with the knowledge gained in this group. Electroejaculation has been applied to men suffering from other neurological conditions. Not only has this included men who have had a retroperitoneal lymph node dissection, but also those suffering from multiple sclerosis, adult diabetes and other non-specific anejaculatory disorders. The levels of injury for the SCI men have ranged from C4 to L4, the majority being in the thoracic area and the injuries being complete. The overall success rate in obtaining an ejaculate, be it antigrade or retrograde has been of the order of 80%. Those suffering from thoracic SCI lesions have had approximately a 90% success rate in obtaining an ejaculate. Of this latter group, some 82% will have an ejaculate considered of sufficient quality for artificial insemination by inter-uterine deposition of washed spermatozoa in vitro fertilization or similar procedure. The range of ages has been from 18 to 49 years of age. Length of time from injury to first electroejaculation procedure has ranged from six months to thirty-six years.

METHOD OF STIMULATION—EXAMPLE #2

Spasticity is a common sequela of spinal cord injury (SCI) with well documented effects on daily activities and increased morbidity. Although there are numerous approaches to the treatment of spasticity, many patients are still unable to find a satisfactory method of managing their spasms with acceptable side effects. In the course of our fertility studies using rectal probe electrostimulation (RPES) in SCI men to produce ejaculation, we observed that a majority of the subjects experienced significant improvement in their spasticity for many hours. this report describes preliminary effort to quantitate this phenomenon in 14 consecutive men treated for anejactulation on 65 occasions in our SCI Fertility Clinic.

Patients eligible for RPES were any men with a history of traumatic SCI who were 18 years of age or older, medically stable, and interested in determining their fertility status. After providing informed consent, subjects had a complete medical history and physical examination with special attention to their neurological and urological status. Laboratory evaluation included a baseline urinalysis, urine culture and sensitivity, complete blood count, FSH, LSH, testosterone and HIV test. Subjects with urinary tract infections were treated with appropriate antibiotics and repeat urinalyses and urine cultures were performed on all subjects on a regular basis.

Rectal probe electrostimulation was performed in the outpatient clinic using the standard procedures we have employed heretofore defined. In brief, these include using a 1⅛ or 1¼-inch diameter rectal probe precision machined from solid bars of PVC. Three linear electrodes lie parallel to the long axis of the probe which was placed in the rectum adjacent to the prostate. Rectal temperature was monitored with a special sensor built into the probe and electrical stimulation was provided by a custom-made electric stimulator designed with isolation transformers and current—limiting devices to prevent accidental delivery of excessive current. As shown in this slide, the treatment variables ranged from 30 volts and 200–500 milliamperes, with a 60 cycles/second sine wave. The number of stimulations varied from 12–35 with each stimulation lasting approximately 1 second and the whole procedure lasted from 5 to 10 minutes.

Prior to each ejaculation session, the subject's bladder was emptied using a sterile catheterization technique and the rectal mucosa was examined with an illuminated rectoscope. As shown in this slide, ejaculation procedures were performed with the subject in the right lateral decubitus position with three staff members present. One person performed the RPES, one monitored blood pressure and collected semen in a plastic cup if antegrade ejaculation occurred. Stimulations were discontinued if the blood pressure exceeded 200 mm Hg systolic or 130 mm diastolic, of ir the subject requested discontinuation because of the side effects or any other reason.

At the end of each ejaculation session, an in-and-out sterile bladder irrigation was performed with a buffered solution to assess the presence of post stimulation sperm in the bladder and a repeat examination of the rectal mucosa was performed. Spasticity was evaluated pre and post RPES using the methods outlined in the next slide. Subjects assessed the frequency of spasms using the Penn Spasticity Scale which ranges from 0 (no spasms) to 4 (spasms occurring more than ten times per hour). They also assessed the interference with self care activity on a 5 point scale with 0 being no interference and 4 being maximum interference which makes the activity very difficult or impossible to perform.

A neurological assessment was performed by one of the authors and included pre and post RPES assessments of the reflexes, the frequency of spasms using the Penn Scale and the Ashworth Scale for assessing the degree of muscle tone. In this scale, 0 indicates no increase in tone and 4 indicates the affected limb is rigid in flexion and extension. The assessments were made prior to the stimulation, within one hour following stimulation and when possible at three hours following the stimulation. Additional assessments by the subject were made throughout the day and then at time of telephone contact 24 hours later. For purposes of this preliminary study, we report only the maximum level of effectiveness (which usually occurred during the first hour after stimulation) and the duration of effectiveness until the subject regained his usual level of tone and spasticity.

RESULTS—EXAMPLE #2

Fourteen male subjects were treated for anejaculation on sixty-five occasions in our SCI Fertility Clinic. Six were quads and four were paras and the mean age was almost 32 years with a range of 22 to 49 years. Time from injury was at most 11 years with a range of 0.5 to 32 years. The level of completeness as reflected in the Frankel Class indicated that six subjects were Frankel A; seven Frankel B, and one was Frankel C.

The overall effectiveness is summarized as follows: Six or roughly 40% expereinced excellent relief of their spasticity as judged by both their personal assessment and the neurological exam. Four or 29% experienced good reduction in spasticity and another 29% experienced no relief at all. The mean duration of effect was 9 hours with a range of 3-24 hours. On occasion, subjects experienced relief from several days up to a week. There was no relation of the effect of RPES on spasticity with the age of the subject, duration of injury, level of injury, completeness of ejaculatory success. Of the six subjects who were taking spasticity medication, all six felt that RPES was more effective than their medications. Those patients who experienced good and excellent relief were essentially flaccid for a number of hours which was a level of relief that none of their medications ever achieved. In addition, subjects noted that RPES was more effective than stretching by physical therapists or use of the Regis machine which produces a short term decrease of spasticity in some subjects. Of the ten subjects who experienced good to excellent reduction in their spasticity, seven said they would be interested in using a home model on a daily basis if available. Subjects who were at risk for dysreflexia all had an evaluation of blood pressure but it was controlled within acceptable limits with a combination of sublingual procardia and/or sublingual nitroglycerine. There were no injuries to the rectal mucosa and subjects did not report any other unpleasant or unacceptable side effects.

The present study builds on the unexpected observation that electrical stimulation provided for another purpose, namely, to produce ejaculation also had a profound effect on the spasticity of the majority of men evaluated. What is of particular interest is the degree of relief experienced by many subjects—in some cases, total flaccidity for many hours—and the length of relief—typically nine hours but in some subjects twenty-four hours or more.

In conclusion, we feel that RPES is effective in reducing spasticity in some spinal cord injured patients. In this group of 14 subjects, spasticity was absent or reduced for a mean period of 9 hours in 71% of the subjects. There was no relation of the effectiveness of the treatment to the patient's age, duration or level of injury, as well as degree of completeness or ejaculatory response. RPES was more effective than medications and there were no unexpected untoward side effects.

We claim:

1. Apparatus for reducing spacticity of neurologically impaired patients comprising:
  a) an elongated anal probe which is adapted to apply stimulus to a patient's pelvic floor, said probe defining a distal penetrating end and a proximal end, an axially aligned channel formed between ends therein with at least three conduits emanating radially therefrom, said probe further defining three longitudinally extending cavities therein, each said cavity being connected to one each of the conduits; three elongated bipolar electrodes, one each being secured in a corresponding cavity and extending above a ventral surface of the probe;
  b) a temperature sensor disposed within one said conduit adjacent one said bipolar electrode, interiorly of the probe;
  c) a stimulator circuit including the bipolar electrodes wherein current in the range of 0–35 volts and 0–700 milliamps may be delivered to the electrodes through the axially aligned channel and conduits alternately by AC or DC, to effect electrical stimulus to the patient whereby to reduce spacticity therein.

2. The apparatus of claim 1 wherein the current is in a 60 Hz sine wave pattern.

* * * * *